United States Patent [19]

Blake

[11] Patent Number: 5,507,806
[45] Date of Patent: Apr. 16, 1996

[54] MULTI-FACETED INTRAOCULAR LENS

[75] Inventor: Larry W. Blake, Coto de Caza, Calif.

[73] Assignee: Pharmacia Iovision, Inc., Irvine, Calif.

[21] Appl. No.: 242,130

[22] Filed: May 13, 1994

[51] Int. Cl.⁶ ............................................ A61F 2/16
[52] U.S. Cl. .......................... 623/6; 606/107; 264/2.7
[58] Field of Search ........................... 623/6; 351/160 R, 351/161; 606/107; 264/2.7

[56]  References Cited

U.S. PATENT DOCUMENTS

| | | | |
|---|---|---|---|
| 2,823,417 | 2/1958 | Pasini et al. | |
| 3,270,099 | 8/1966 | Camp | |
| 3,339,997 | 9/1967 | Wesley | |
| 3,440,306 | 4/1969 | Neefe | |
| 3,560,598 | 2/1971 | Neefe | |
| 3,693,301 | 9/1972 | Lemaitre | |
| 3,866,249 | 2/1975 | Flom | 623/6 |
| 3,950,082 | 4/1976 | Volk | |
| 4,010,496 | 3/1977 | Neefe | 623/6 |
| 4,104,339 | 8/1978 | Fetz et al. | |
| 4,110,848 | 9/1978 | Jensen | 623/6 |
| 4,121,885 | 10/1978 | Erickson et al. | |
| 4,179,484 | 12/1979 | Neefe | |
| 4,198,714 | 4/1980 | Jensen | 623/6 |
| 4,373,218 | 2/1983 | Schachar | 623/6 |
| 4,418,991 | 12/1983 | Breger | 351/161 |
| 4,450,593 | 5/1984 | Poler | 623/16 |

(List continued on next page.)

FOREIGN PATENT DOCUMENTS

| | | |
|---|---|---|
| 2556665 | 6/1977 | Germany |
| 2725219 | 12/1978 | Germany |

OTHER PUBLICATIONS

Peter Hoefer, Translation of German Patent No. 25 56 665, Issued Jun. 30, 1977, pp. 1–9.
Peter Hoefer, Translation of German Patent No. 27 25 219, Issued Dec. 14, 1978, pp. 1–12.
Sean Henahan, "Early Trials Show No Blurring Of Vision With Multifocal IOL," *Ophthalmology Times*, Aug. 15, 1988, p. 27.
Tim Donald, "Silicone Demonstrates Suitable Optic Characteristics In Resolution Testing," *Ocular Surgery News*, vol. 6, No. 16, Aug. 15, 1988, pp. 1, 16–17.
Tom Waters, "Personal Tech 3–D Comes Home," *Discover*, May 1988, pp. 30–32.
Jayne B. Morehouse, "Resolution Efficiency In Water Supported As New IOL Standard," *Opthalmology Times*, Apr. 15, 1987, pp. 46, 48.
3M Health Care Group, "The 3M Multifocal IOL," *3M HealthCare*, pp. 1–4.
"The Shah Bifocal Universal MK II Intra Ocular Lens." Norman S. Jaffe et al., "Pseudophakos," published by the C. V. Mosby Company, 1978. Chapter 6, pp. 58–60.
"Ocular Surgery News," Jun. 1, 1987, vol. 5, No. 11, pp. 1, 14 and 15. Article No Near Corrections Needed By Almost 50 in Bifocal IOL Series.
Ocular Surgery News, Jun. 1, 1987, vol. 5, No. 11, pp. 1, 12 and 13. Article "Bifocal IOL Implanted in England; U.S. Trial May Begin This Month."

*Primary Examiner*—Mary Beth Jones
*Attorney, Agent, or Firm*—Knobbe, Martens, Olson & Bear

[57]  ABSTRACT

An improved multi-faceted intraocular lens with a main optical element having a plurality of optical elements. The flexible, thin multi-faceted intraocular lens is made of an optical-grade soft biocompatible material, such as a flexible acrylic material, a hydrophilic material, or a silicone material. The thin, flat, multi-faceted intraocular lens may enable implantation of the lens through an intraocular lens injector having an injection tube with a diameter of approximately 1 mm to 4 mm. The plurality of optical elements each may have the same or differing diopter powers. Additionally, the plurality of optical elements may be aligned to form a multi-focal lens. Further, the optical elements each may be selected from a group consisting of toric elements, aspheric elements, and spherical elements depending upon the type of correction desired. Lastly, the multi-faceted intraocular lens may be effective in the treatment of age-related macular degeneration.

2 Claims, 13 Drawing Sheets

U.S. PATENT DOCUMENTS

| | | | |
|---|---|---|---|
| 4,504,982 | 3/1985 | Burk | 623/6 |
| 4,512,040 | 4/1985 | McClure | 623/6 |
| 4,573,998 | 3/1986 | Mazzocco | 623/6 |
| 4,615,702 | 10/1986 | Koziol et al. | 623/6 |
| 4,619,662 | 10/1986 | Juergens, Jr. | 623/6 |
| 4,640,595 | 2/1987 | Volk | 351/160 R |
| 4,659,524 | 4/1987 | Neefe . | |
| 4,666,446 | 5/1987 | Kozol et al. | 623/6 |
| 4,673,406 | 6/1987 | Schlegel | 623/6 |
| 4,701,288 | 10/1987 | Cook et al. . | |
| 4,702,244 | 10/1987 | Mazzocco | 623/6 X |
| 4,710,193 | 12/1987 | Volk | 623/6 |
| 4,731,078 | 3/1988 | Stoy et al. | 623/6 |
| 4,752,123 | 6/1988 | Blaker | 351/161 |
| 4,753,520 | 6/1988 | Silvergate . | |
| 4,753,653 | 6/1988 | Bissonette et al. | 623/6 |
| 4,759,762 | 7/1988 | Grendahl | 623/6 |
| 4,769,033 | 9/1988 | Nordan | 623/6 |
| 4,895,585 | 1/1990 | Angenet et al. . | |
| 4,898,461 | 2/1990 | Portney . | |
| 4,906,245 | 3/1990 | Grendall | 623/6 |
| 4,917,681 | 4/1990 | Nordan | 623/6 |
| 5,074,877 | 12/1991 | Nordan | 623/6 |
| 5,133,749 | 7/1992 | Nordan | 623/6 |
| 5,147,393 | 9/1992 | Van Noy et al. | 623/6 |
| 5,326,348 | 7/1994 | Nordan | 623/6 |

 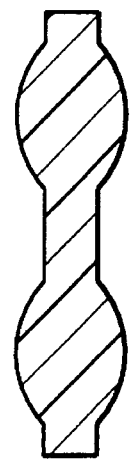
FIG. 20  FIG. 21
 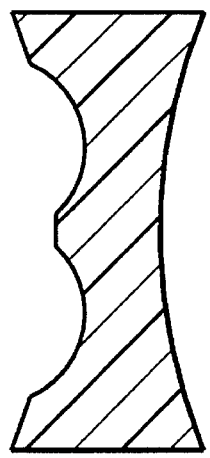 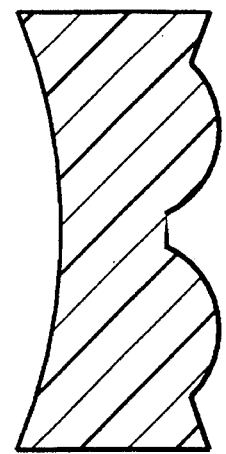
FIG. 22  FIG. 23  FIG. 24
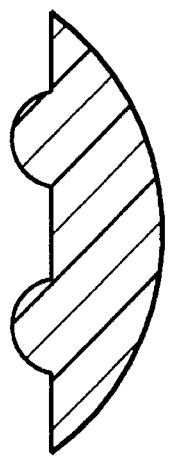 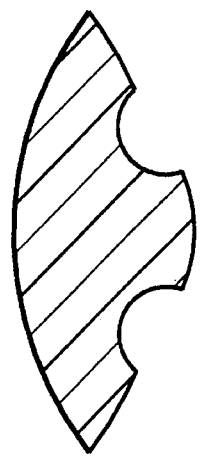
FIG. 25  FIG. 26

MULTI-FACETED INTRAOCULAR LENS

BACKGROUND OF THE INVENTION

1. Field of the Invention

The present invention relates to the field of intraocular lens replacement and, more particularly, to an intraocular lens which comprises a multitude of optical surfaces.

2. Description of the Related Art

Artificial intraocular lenses, used to replace damaged or diseased natural lenses in the eye, have been widely accepted in the last several decades. Typically, such intraocular lenses comprise some type of optical element and a support, or haptic, coupled thereto for properly positioning and centering the intraocular lens within the eye. Previously, many such lenses were made from polymethylmethacrylate (PMMA), a hard plastic composition. More recently the use of a soft, biocompatible material, such as silicone, to manufacture the lenses is more common. Silicone lenses have the advantage of being lighter in situ than PMMA lenses, and because they are flexible, they can be folded or rolled to reduce their size during implantation into the eye in accordance with conventional surgical procedures.

A technique that has gained wide acceptance for the removal of the diseased or damaged native lens is called phacoemulsification. The phacoemulsification process is very advantageous because of the extremely small incision required to perform the technique. The incision can be as small as 2 mm in length. It is desirable to insert an artificial intraocular lens into the patient's eye to replace the native lens of the eye after the phacoemulsification procedure has been completed. With the latest advances in surgical procedures performed on the lens capsule, such as a capsulorexis procedure, it is possible to remove the native lens of the eye while maintaining the lens capsule almost entirely intact. The capsulorexis procedure enables a small curvilinear tear to be made in the lens capsule through which the artificial lens is implanted. The small opening in the lens capsule through which the intraocular lens is loaded and pushed further enhances the desirability of a pliable lens that can be inserted into the small capsulorexis opening. By maintaining the lens capsule intact and inserting the artificial lens into the lens capsule, a more natural lens replacement can be achieved. It is desirable to enable the insertion of the intraocular lens into the eye without requiring the elongation of either the phacoemulsification incision or the capsulorexis opening.

A lens injector is traditionally used to insert a single-piece intraocular lens, which is loaded into the injector and then inserted into the eye. The use of a lens injector to insert a compressed lens is desirable because the small phacoemulsification incision does not require elongation. In addition, the insertion procedure is significantly simplified by the loading and insertion features of an intraocular lens injector. In addition, the entire lens is contained within an insertion tube until the lens is injected into the lens capsule, thereby reducing the likelihood of damaging the surrounding eye tissue while the lens is being inserted. The simplification of the insertion procedure utilizing an intraocular lens injector has increased the frequency of their use. As the use of lens injectors for the insertion of an intraocular lens has increased, the demand for single-piece intraocular lens designs, which are compatible for use with lens injectors, has also increased.

In order to reduce trauma to the surrounding eye tissue caused by the lens injector, it is desirable that the diameter of the insertion tube of the injector be minimized. However, the thickness of the intraocular lens that is loaded, rolled and pushed through the injector is often the limiting factor in the intraocular lens injector design, as the insertion tube must be able to contain the entire lens in its loaded state. Thus, in order to enable the use of a smaller intraocular lens injector, the thickness of the intraocular lens itself must be reduced without altering the optical properties of the lens.

Further, it is desirable to provide an intraocular lens which can be adapted to correct a number of vision related problems. For example, over 30% of Americans over the age of 75 are affected by age-related macular degeneration (AMD). Further, age-related macular degeneration has become the leading cause of vision loss among the elderly. Age-related macular degeneration is a disease that effects the retina in the eye of older adults, causing central visual field loss which can result in reduced visual acuity. Other diseases of the retina, such as retinitis pigmentosa, cause portions of the retina to become non-functional. Therefore, it would be advantageous to develop an intraocular lens that could enhance the vision of patients who suffer for age-related macular degeneration and other retina related visual impairments. Finally, many intraocular lens patients complain about their inability to focus on both near and distant objects. It would be desirable to provide an intraocular lens that would enable an intraocular lens patient to focus on both close and distant objects.

SUMMARY OF THE INVENTION

A preferred embodiment of a multi-faceted intraocular lens comprises a first optical element, aligned along a first optical axis and a second optical element aligned along a second optical axis which is not coincident with said first optical axis. In a preferred embodiment, each of the first and second optical axes are parallel. Preferably, the first and second optical elements transmit an image onto first and second locations of the retina, respectively. In one embodiment of the invention, the first and second optical elements have the same diopter power. In another embodiment, the first and second optical elements have differing diopter powers. The first and second optical elements preferably are on the same optical plane. In a preferred embodiment, the first and second optical elements are selected from a group consisting of toric elements, aspheric elements, and spherical elements. Preferably, the first and second optical elements are formed by molding the lens in a coined multi-faceted intraocular mold. Further, the intraocular lens also comprises a haptic support portion.

In one embodiment, the intraocular lens is a soft single-piece lens made from an optical-grade soft elastomeric biocompatible material, such as a flexible acrylic material a hydrophilic material, or a silicone material. Preferably, silicone is used to form a preferred embodiment of the intraocular lens. A preferred embodiment of a single-piece multi-faceted intraocular lens comprises an optical element and a flat haptic support portion. The single-piece multi-faceted intraocular lens is able to compress or roll-up into a cylinder of an extremely small diameter. The diameter of the thin rolled-up multi-faceted lens preferably enables implantation of the lens via an intraocular lens injector having an injection tube of a 3–4 mm diameter. More preferably, the diameter of the thin rolled-up multi-faceted lens preferably enables implantation of the lens via an intraocular lens injector having an injection tube of a 2–3 mm diameter, or even as small as 1 mm in diameter.

The plurality of optical elements on the intraocular lens may be aligned to form a multi-focal lens. In such an embodiment, the first and second optical elements lie along an annular ring around a central portion of the intraocular lens. The annular ring of optical elements is used to provide a multi-focal lens by focusing all of the light rays that are incident on the annular ring of optical elements to one focal point on the retina and the light rays which are incident upon a central portion of the intraocular lens are focused onto another focal point on the retina.

Lastly, the multi-faceted intraocular lens may be effective in treatment of age-related macular degeneration (AMD). In those patients suffering from AMD, the central portion of the retina is damaged. In one embodiment of the multi-faceted intraocular lens, a first optical element is positioned and aligned to form an image on a first location on a retina of a patient; and a second optical element is positioned and aligned to form an image on a second location on a retina of a patient. Therefore, it is possible to treat AMD by providing a patient with a multi-faceted intraocular lens as described above. The multi-faceted intraocular lens is inserted into an eye of the patient replacing their natural crystalline lens. One method of treating age-related macular degeneration, comprises the steps of transferring plural images of an object onto different locations on the retina. In a preferred embodiment, at least one of said plural images of said object is transferred onto non-central portion of the retina. By providing the patient with a lens that transfers the image incident upon the lens onto a plurality of locations of the retina, preferably the noncentral portions of the retina which are healthy will receive at least one of the transmitted images from the lens. These noncentral portions of the retina will be able to process the image and will enable the patient to regain functional use of the remainder of their vision.

These and other features and advantages of the present invention are set forth more completely in the accompanying drawings and the following description.

BRIEF DESCRIPTION OF THE DRAWINGS

FIG. 20 is a cross-sectional view of a main optical element having a plurality of convex optical elements on one side of the optical element.

FIG. 21 is a cross-sectional view of a main optical element having a plurality of convex optical elements on each side of the main optical element.

FIG. 22 is a cross-sectional view of a main optical element having two concave optical elements on one side of the main optical element.

FIG. 23 is a cross-sectional view of a biconcave main optical element having a plurality of concave optical elements on one side of the main optical element.

FIG. 24 is a cross-sectional view of a biconcave main optical element having two convex optical element portions on one side of the main optical element.

FIG. 25 is a cross-sectional view of a convex main optical element having a plurality of convex optical elements on one side of the convex main optical element.

FIG. 26 is a cross-sectional view of a convex main optical element having a plurality of concave optical elements on one side of the convex main optical element.

DETAILED DESCRIPTION OF THE PREFERRED EMBODIMENTS

Figure 1:
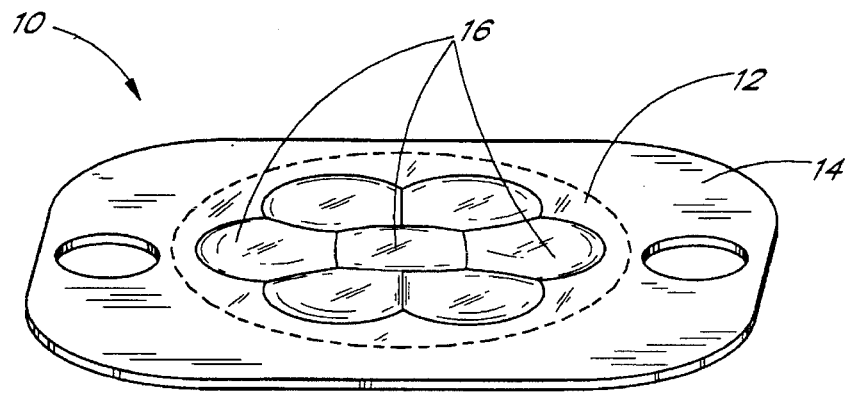
FIG. 1 is a perspective view of a single-piece multi-faceted intraocular lens.

A preferred embodiment of the present invention comprises a single-piece flexible, multi-faceted intraocular lens 10, as illustrated in FIG. 1. The single-piece intraocular lens 10 comprises a main optical element 12 and a haptic, or support portion, 14. The main optical element 12 preferably comprises a plurality of optical elements 16, i.e., is a multi-faceted main optical element 12. Preferably, the optical elements or optical zones of the lens have optic axes which are not coincident with each other. Desirably, the optical elements have optical axes which are parallel to each other. Further, the optical elements 14 are located on the same lateral optical plane. The thickness of the main optical element 12 is attributed to the sagittal thickness of the optical elements 16 and the thickness of the haptic portion 14. Preferably, the diameter of the optical elements 16 is between approximately 1.0 mm and 3.0 mm. In one embodiment, the diameter of the optical elements 16 may be as small as approximately 0.1 min. Advantageously, the optical elements 16 are extremely thin and do not suffer from the spherical aberration of a more traditional full optical diameter optical element even if the optical elements 16 are spherical in shape. The optical elements 16 are positioned tangential to each other and cover a central portion of the main optical element 12. The flat intraocular lens 10 is comprised of a soft optical-grade biocompatible material, such as a flexible acrylic material, a hydrophilic material, or a silicone material. Preferably, silicone is used to from the flexible single-piece lens 10.

Figure 2:
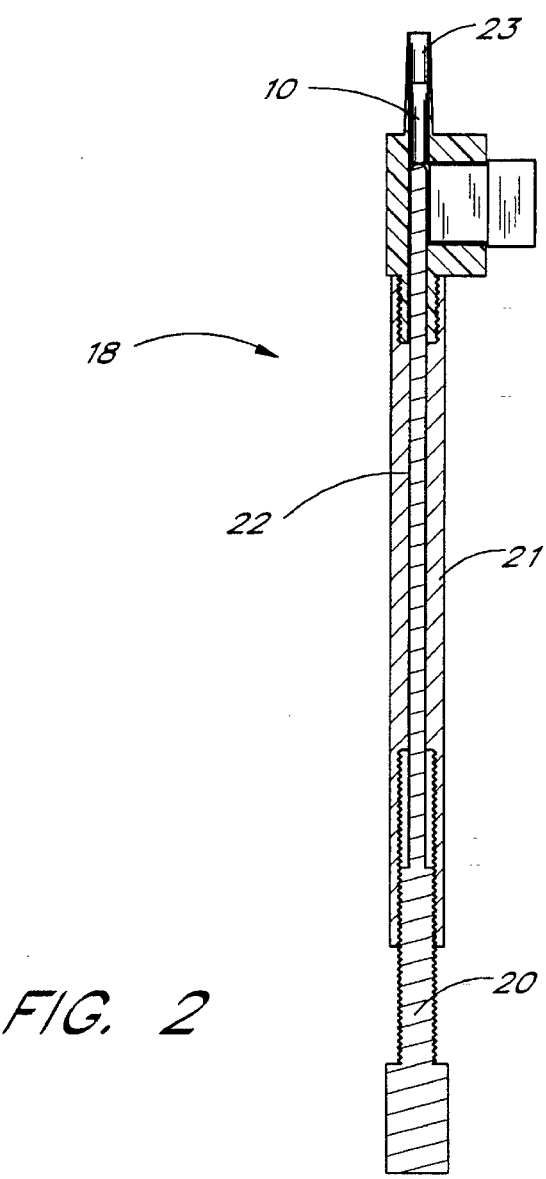
FIG. 2 is an cross sectional view of an intraocular lens injector and a rolled-up single-piece multi-faceted intraocular lens.

The flat single-piece lens 10 is designed for use with an intraocular lens injector 18, as illustrated in FIG. 2. The intraocular lens injector 18 preferably comprises an insertion rod 20, a main body 21 and an insertion tube 22. Preferably, the insertion tube 22 has an extremely small diameter. As describe above, the limiting factor of the insertion tube diameter is the thickness of the lens that is rolled up and contained within the insertion tube 22. The thin single-piece multi-faceted lens 10 can be compressed or rolled up and inserted into the insertion tube 22 of the intraocular lens injector 18. Importantly, the diameter of the insertion tube 22 is minimized by utilizing the single-piece multi-faceted intraocular lens 10 of the preferred embodiment such that the end 23 of the insertion tube 22 can be placed through a conventional phacoemulsification incision and a capsulorexis opening without damaging the surrounding tissue. In a preferred embodiment, the intraocular lens injector 18 is made from metal. The thickness of the insertion tube wall required to provide structural integrity to the injector 18 is relatively thin when metal is used to form the injector 18. Assuming the thickness of the main optical element 12 of the single-piece lens 10 is approximately 0.5 mm and the insertion tube 22 is made from metal, the lens injector 18 has an insertion tube 22 with an end 23 as small as 1 mm. In an alternate embodiment, the insertion tube 22 of the intraocular lens injector 18 is made from plastic. Plastic requires a slightly larger wall thickness than metal to provide the required structural integrity of the lens injector 18. Assuming the thickness of the main optical element 12 of the single-piece lens 10 is approximately 0.5 mm and the insertion tube 22 is made from plastic, the lens injector 18 has an insertion tube 22 with an end 23 as small as 1.5 mm. Preferably, the intraocular lens 10 is capable of being rolled-up and inserted into an intraocular lens injector 18 having an injection tube with a diameter of approximately 1 mm to 4 mm.

Figure 3:
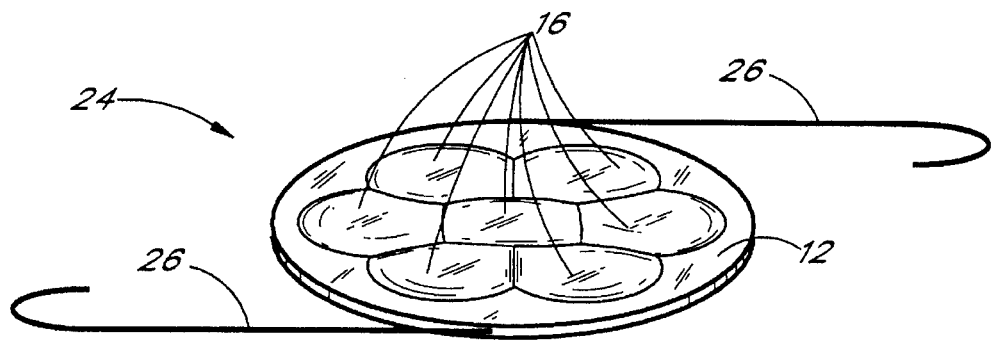
FIG. 3 is a perspective view of a multi-piece multi-faceted intraocular lens.

An alternate embodiment of the intraocular lens of the present invention is a multi-piece intraocular lens 24. The multi-piece intraocular lens 24, as illustrated in FIG. 3, comprises a main optical element 12 and haptic portions 26. The main optical element 12 of the multi-piece lens 24 is similar to the main optical element 12 of the single-piece intraocular lens 10 and comprises a plurality of optical elements 16. The haptic portions 26, each secured to the main optical element 12 on diametrically opposed sides, aid in centering the lens 20 within the eye after implantation. Preferably, the haptic portions 26 are formed from silicone and are bonded to the main optical element 12.

Figure 4:
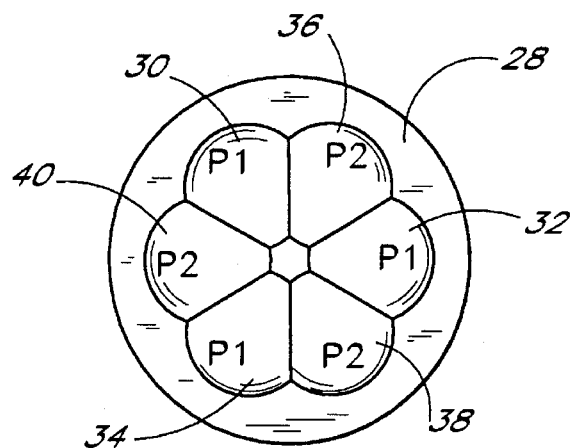
FIG. 4 is a schematic top plan view of a main optical element with a plurality of optical elements having differing diopter powers thereon.

FIG. 4 illustrates a close-up view of one embodiment of main optical element 28 having a plurality of optical elements 30–40 positioned to intersect each other. Alternating optical elements 30–40 have differing diopter powers. For example, optical elements 30, 32, and 34 each has a diopter power of P1, whereas optical elements 36, 38, and 40 each has a diopter power of P2. As will be understood by those of skill in the art, each optical element 30–40 individually focuses the image which it receives onto the retina of the eye. By juxtaposing a plurality of optical elements 16 with alternating diopter powers as illustrated in FIG. 4, the image will be transferred onto a plurality of positions on the retina. It is believed that the human brain will be able to integrate the plurality of images focused onto the retina into a functional image.

Figure 5:
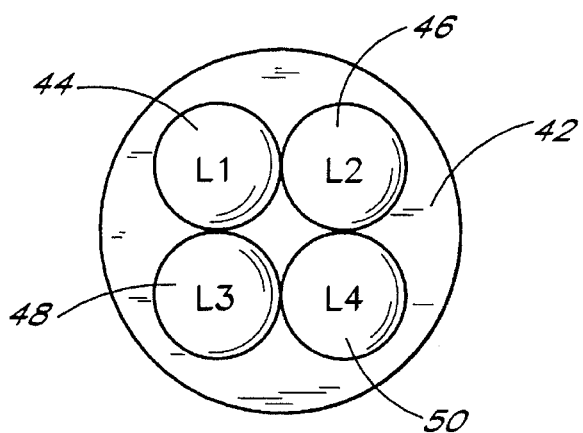
FIG. 5 is a schematic top plan view of a main optical element with a plurality of optical elements having differing optical shapes thereon.

FIG. 5 illustrates another alternate embodiment of an optical element 42 comprising a plurality of optical elements 44–50. Each of the optical elements 44–50 are positioned tangential to each other and cover a central portion of the optical element 42. Each of the optical elements 44–50 may include optics of different shapes and diopter powers. In a preferred embodiment, all of the optical elements 44–50 are located on the same optical plane. Preferably, each of the optical elements 44–50 are selected from a group of optical element shapes consisting of toric elements, aspheric elements, and spherical elements. For example, optical element 44 has a lens shape L1; optical element 46 has a lens shape L2; optical element 48 has a lens shape L3; and optical element 50 has a lens shape L4. Each of the lens shapes L1–L4 illustrated in FIG. 5 are schematic views of optical elements having differing lens shapes. As will be apparent to one of skill in the art, each optical element can be selected to be of any optical element shape, depending upon the type of correction to the light rays incident on that portion of the optical element 42 that is desired.

Figure 6:
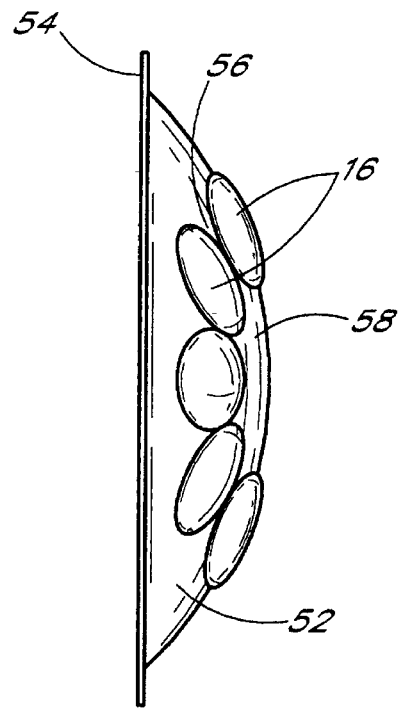
FIG. 6 is a perspective view of a bio-convex main optical element with a plurality of optical elements thereon.

Additionally, optical elements can be added to an optic of a conventional design to add additional power factors or focal point correction to the optic. For example, as illustrated in FIG. 6, a main optical element 52 of a conventional biconvex spherical lens 54 additionally comprises an annular ring 56 of optical elements 16 on one side of the main optical element 52. The annular ring 56 of optical elements 16 is used to provide a multi-focal lens by focusing all of the light rays that are incident on the annular ring 56 of optical elements 16 to the same focal point as the light rays which are incident upon a center 58 of the optical element 52. As is known to one of skill in the art, light which is passed through the cornea of the eye is pre-focused by the cornea and consists of an approximate 12 degree cone angle of light. Preferably, the plurality of optical elements 16 that comprise the annular ring 56 are oriented on a similar 12-degree convergent angle. The alignment of the convergent angle of the optical elements 16 on the annular ring 56 with the cornea assists in the focusing of the light rays from both near and distant locations into a single focal point on the retina of the eye. Further, optical elements 16 can be added to a main optical element 52 of any other conventional lens shape, such as an aspheric or a toric optical element. Preferably, each of the optical elements 16 can be selected from a group of optical element shapes consisting of toric elements, aspheric elements, and spherical elements. In addition, each of the optical elements 16 may comprise any of a number of different diopter powers. Lastly, each of the optical elements 16 may be placed in any location on the main optical element 52 to focus the incoming light rays as desired.

In a preferred embodiment, an intraocular lens with an optic having a plurality of optical elements is formed by a molding process. In order to form a mold with the desired plurality of optical elements, the mold is made by a coining process as described in U.S. Pat. No. 5,104,590 issued Apr. 14, 1992, entitled "Fabrication of an Intraocular Lens", which is hereby incorporated by reference. The pattern, or reverse mold is transferred onto a coining mandrel utilizing a CNC machine. Preferably, if the optical element surface is a mono-focal surface, the pattern is transferred utilizing optical lapping and polishing techniques known to those of skill in the art. More preferably, if the optical element surface is an aspheric surface, a multi-focal surface or has an unusual or complex surface design, the pattern is transferred utilizing typical CNC machining procedures which are known to those of skill in the art. In the case when the main optic comprises a plurality of optical elements each with a different diopter power and/or shape, a plurality of patterns are formed, each pattern having the shape of one of the plurality of different optical shapes and/or diopter powers of each optical element. As is well known to one of skill in the art, the radius of curvature of an optical element is proportional to the focal length of that element. As a radius of curvature of an optical element decreases, the diopter power, which is defined as the inverse of the focal length when measured in meters, increases.

The replica formed by the CNC machine is to be used as a coining mandrel for coining one or more optical surfaces onto the mold cavity. It is to be understood that the term coining is used to define the permanent deformation of a soft material, as impressed by a harder material. Preferably, the replica, or coining mandrel, is a small, cylindrical piece of high-grade hardened alloy tool steel, capable of reaching a hardness of 58–65 Rockwell, scale C ($R_c$). Most preferably, D-2 steel is used. Once the coining mandrel has been lathed, milled or ground with a reproduction of the pattern utilizing CNC technology, the rough edges developed during the replication process are polished off. Significantly, the peripheral edge of the coining mandrel is radiused such that when an optical mold is coined, the convexity of the resultant mold cavity will yield a smooth radius product.

Figure 7:
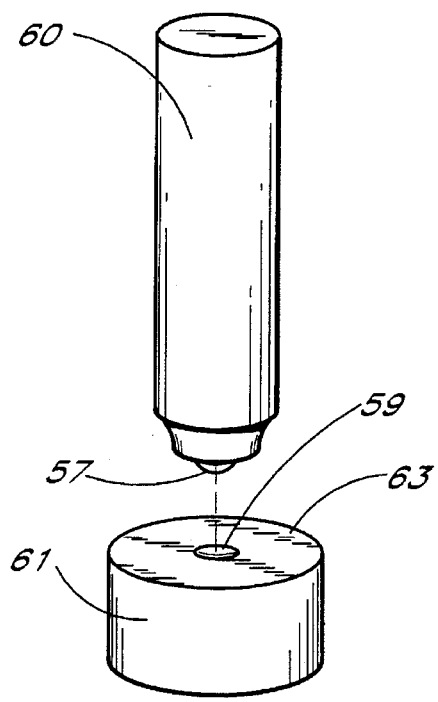
FIG. 7 is a perspective view of a coining mandrel and a mold blank used in the formation of a multi-faceted intraocular lens mold.

The coining mandrel 60, illustrated in FIG. 7, is then heat treated in an oven to harden the D-2 steel throughout to a hardness of between 58 to 65 Rockwell, scale C ($R_C$), and most preferably, 63 $R_C$, which corresponds to a tensile strength of 320,000 psi. Because oxygen tends to leave an undesirable coating on the surface of the steel during the heat-treating process, which would have to be sandblasted off, the coining mandrel is preferably hardened in one of two ways. The preferred way is to evacuate the air out of the oven to produce a vacuum environment and heat the coining mandrel by radiation to approximately 1300° F. The coining mandrel is then allowed to slowly cool and will emerge from the oven within the desired range of hardness. As the steel is heated and cooled, its grain structure changes in a predictable manner. Another way of heat treating the coining mandrel to a hardness of between 58 and 65 $R_C$ is to heat it in a nitrogen oven. This process is much slower than the vacuum method, as the coining mandrel is heated primarily by convection, rather than by radiation.

During the heat treating process, the hardness, strength, and wear resistance of the coining mandrel are increased; however, nicks, scratches, and impurities in the steel are also magnified. Thus, once the coining mandrel has been heat treated and hardened to 58 to 65 $R_C$, the reverse mold surface must be polished to an optical surface. The general practice is to polish the surface of the mandrel with a succession of polishing agents, progressing from a course grit to a finer grit. Because of the nature and intended use of the corning mandrel, as well as the minute surface area of the reverse mold surface, the coining mandrel must be machined and then hand polished under a microscope by methods known to those of skill in the art.

Polishing the surface of the coining mandrel 60 is a very tedious process and requires hours of meticulous work. The first step in the optical polishing of the coining mandrel is to remove all the crowns and crests from the surface, which were magnified during the hardening process. This is accomplished by applying a small amount of fine machine oil and 600-grit silicone carbide material to the surface of the coining mandrel and polishing it with small, circular motions, using the end of a brass rod, followed by the use of 1000-grit silicone carbide. To ensure that the surface of the coining mandrel is not being over polished and that the precise calculated radii of curvature are maintained, a comparator is used during each step. Once the crowns and crests have been polished off the surface of the coining mandrel, machine oil and aluminum oxide ($Al_2O_3$), having a grit size of 1 micron (1 μ), is employed as a polishing agent, and the surface of the coining mandrel is further hand polished with wood sticks in small, circular motions. Next, using a handheld polishing machine having a hardened felt surface, the coining mandrel is optically lapped using 0.3 μ $Al_2O_3$ and fine machine oil. Finally, the coining mandrel is tumbled in a standard tumbler, as commonly used in the field to tumble and polish intraocular lenses. The tumbler is filled with 1 mm and 2 mm glass beads, fine machine oil of the type used during the above polishing steps, an anti-settling agent, and mineral spirits. Preferably, the anti-settling agent is fumed silicone dioxide, having a particle size of between 0.7 to 2.7 angstroms (Å), as made commercially available under the name Cab-O-Sil fumed silica. The fumed silica is used as a suspending or anti-settling agent in the tumbler and accelerates the polishing process during tumbling. In addition, it is noteworthy that tumbling media, such as water or alcohol, are not suitable for use in the tumbler when polishing the coining mandrel, as these agents would cause electrolysis, which in turn, would etch the surface of the coining mandrel. Upon cessation of the tumbling process, the coining mandrel should emerge having a highly polished optical surface of the desired configuration. A final hand lapping process utilizing a 0.1 μ diamond compound and a soft textile surface, such as a lint free polyester or cotton textile, completes the polishing process.

FIG. 7 illustrates a hardened coining mandrel 60 with a polished surface 57, which is to be used to stamp its impression into a mold blank 61 to form one-half of a lens mold. Preferably, the mold blank 61 is made of a material softer than the material from which the coining mandrel 60 is made. Further, the mold blank 61 preferably has an optical finish on the face 63 thereof; so as to form an optical power surface. An optical power surface is one that is contoured to focus light rays so that they converge or diverge to form an image. As the coining mandrel 60 has been hardened to 58 to 65 $R_C$, the choice of softer materials would appear endless. However, in the interest of making a long-lasting mold, any grade of good-quality stainless steel is used. Preferably, the mold blank 61 is formed of either a 200 series, 300 series or a 400 series stainless steel. Presently, a 400 series vacuum process stainless steel is preferred, with 410 or 420 stainless steel proving well suited.

The mold blank 61 is machined in the desired shape and thickness, and the face 63 is optically lapped in a manner which is well known in the art. Preferably, the face 63 of the mold blank 61 is polished in a series of steps, beginning with 300-grit sandpaper and oil and proceeding to finer grades of sandpaper, having grit sizes of 400 and 600. The mold blank 61 is then polished using a lapping plate, having a urethane felt cover or optical wax surface using a 1 μ sapphire ($Al_2O_3$) and water slurry. Finally, the face 63 of the mold blank 61 is optically finished with a rotary polisher, having a urethane felt cover in a 0.3 μ $Al_2O_3$ and water slurry.

Figure 8:
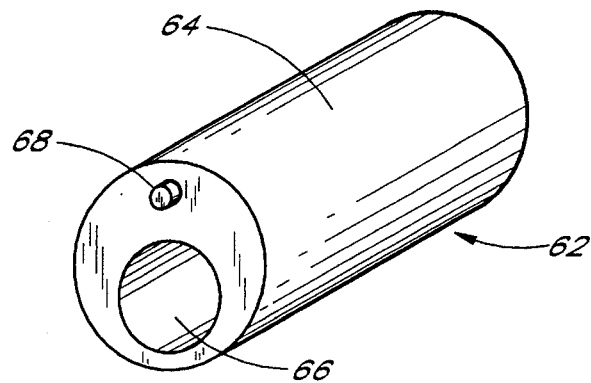
FIG. 8 is a perspective view of a coining mandrel positioning device.

Following the optical polishing of the face 63 of the stainless steel mold blank 61, a cavity 59 is formed by pressing the mandrel 60 into the face 63 of the mold blank 61. FIG. 8 illustrates a mandrel-positioning device 62. The mandrel-positioning device 62 is a stainless steel cylinder sized to have an equivalent diameter as the mold blank 61. The mandrel-positioning device 62 comprises a main body 64 with a circular bore 66 offset from the center of the positioning device 62 and having an inner diameter sized to receive and align the coining mandrel 60 (FIG. 7). Further, the mandrel-positioning device 62 comprises a positioning pin 68 aligned with the mandrel-holding bore 66. The mandrel-positioning device 62 is used to align a coining mandrel 60 with the mold blank 61 in order to form a plurality of cavities on the surface of the mold blank 61 which are used to form the optical elements of the lens.

Figure 9:
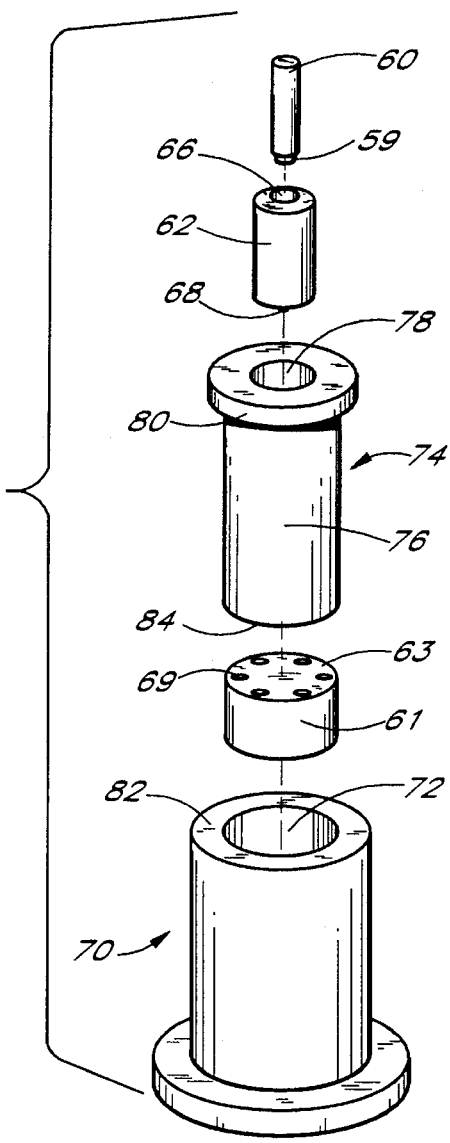
FIG. 9 is an exploded perspective view of a mold forming assembly, used in the fabrication of a multi-faceted intraocular lens mold.

In order to form six tangentially aligned optical elements, six alignment holes 69 are drilled in the outer perimeter of the mold blank 61, as illustrated in FIG. 9. The six alignment holes 69 mate with the positioning pin 68 on the mandrel-positioning device 62 and are located in line with the desired location of cavities which form the optical element on the mold blank 61. As shown in FIG. 9, hardened drill or mold bushings are utilized to maintain the relative location of the coining mandrel-positioning device 62 with respect to the polished mold blank 61. Preferably, the bushings are formed of tool steel, as they will ultimately be subjected to exceptionally high loads. An outer bushing 70 is cored and has an inner diameter 72 sized to receive and align the polished mold blank 61 with minimal clearance about the periphery thereof, so as to ensure that the mold blank 61 will not move during the mold-formation process. Similarly, an inner bushing 74 is also cored having an outer diameter 76 selected such that the inner bushing 74 will be centered with respect to the outer bushing 70 and an inner diameter 78 for aligning the coining mandrel-positioning device 62 with respect to the mold blank 61. The inner bushing 74 is further equipped with a flange 80 adapted to rest upon an upper rim 82 of the outer bushing 70 to maintain a small gap between a bottom surface 84 of the inner bushing 74 and the mold blank 61.

To form a cavity in the mold blank 61, the outer bushing 70 is placed on a hardened surface. The mold blank 61 is inserted into the core of the outer drill bushing 70 with the polished face 63 of the mold blank 61 facing upwards. It is important to execute care in the insertion of the mold blank 61 into the bushing 70, as scratches on the surface 63 of the blank 61 may result in a cavity that yields flawed lenses. The inner bushing 74 is then inserted into the core 66 of the outer bushing 70, so that the flange 80 rests on the upper rim 82 of the outer drill bushing 70. The coining mandrel-positioning device 62 is lowered into the core of the inner bushing 74, such that the positioning pin 68 on the coining mandrel-positioning device 62 is inserted into one of the positioning holes 69 on the mold blank 61 until the coining mandrel-positioning device 62 just touches the surface 63 of the mold blank 61. Finally, the coining mandrel 60 is lowered into the core of the coining mandrel-positioning device 62 until the surface 59 of the coining mandrel 60 just touches the surface 63 of the mold blank 61. A second hardened surface (not shown) is carefully set on top of the coining mandrel 60 and the coining mandrel-positioning device 62, and the formation assembly is put into a hydraulic press (not shown).

It is noteworthy that the coining mandrel 60 and coining mandrel-positioning device 62 should extend outward above the flange 80 of the inner bushing 74 by an amount equal to the desired final depth of the mold cavity, taking into account the amount of compression, or shrinkage, of the coining mandrel expected during depressing of the mold cavity. Preferably, the coining mandrel 60 extends above the flange to accommodate the sagittal distance of the optical element as determined by the desired diameter of the optical surface plus a compression correction factor. The compression correction factor is proportional to the load applied to the coining mandrel 60 as will be understood by those of skill in the art. To ensure proper deformation of the mold cavity, the hydraulic press is loaded to provide a pressure in excess of 250,000 psi upon the surface of the coining mandrel 60. In order to allow for the creeping of the materials, the press remains under full load for approximately 15 minutes after the gap disappears. Despite the high pressure applied to the coining mandrel 60, the coining mandrel 60 is not deformed beyond the elastic limit of the material, and therefore returns to its original form upon removal of the load. Unlike the coining mandrel 60, the stainless steel mold blank 61 has a much lower yield strength, and therefore undergoes permanent deformation upon application of the load. Thus, not only does the newly formed mold half exhibit a mold cavity (FIG. 10) having a reverse imprint of the surface 59 of the coining mandrel 60 at the desired depth, but also undergoes a radial expansion, resulting in an interference fit within the core of the outer bushing 70, as well as a slight eruption about the periphery of the mold cavity. After the load has been removed, the coining mandrel 60 and the coining mandrel positing device 62 are lifted from the formation assembly.

In order to form the imprint of the other optical elements on the surface 63 of the mold blank 61, the positioning pin 68 on the coining mandrel-positioning device 62 is aligned with another one of the alignment holes 69 on the mold blank 61. A coining mandrel-positioning device 62 is again lowered into the core of the inner bushing 74 while the positioning pin 68 is inserted into the corresponding alignment hole 69 in the mold blank 61 until the coining mandrel positioning device 62 touches the surface 63 of the mold blank 61. Finally, the coining mandrel 60, having the same or differing surface impression 59 as the previous coining mandrel is lowered into the core 66 of the coining mandrel-positioning device 62 until the surface impression 59 of the coining mandrel 60 also touches the surface 63 of the mold blank 61. As described above, a second hardened surface is carefully set on top of the coining mandrel 60 and the formation assembly is put into a hydraulic press (not shown). The above procedure is repeated until the positioning pin 68 on the coining mandrel-positioning device 62 has been placed into each of the alignment holes 69 on the mold blank 61. If desired, a coining mandrel 60 can be positioned in the center of the inner bushing 74 until it touches the center of the mold blank 61 in order to form a central optical element. As described above, the mold 61 is placed into a hydraulic press and the coining mandrel 60 is pressed into the mold cavity.

After the load has been removed, the coining mandrel 60, the coining mandrel positing device 62 (if used) and the inner bushing 74 are lifted from the formation assembly. The pressed mold blank 61, however, must be forced out of the outer bushing 70 due to the interference fit caused by the radial expansion of the mold blank 61. Significantly, during the mold forming process, slight imperfections present on the surface 63 of the mold blank 61 in the localized area of the mold cavity are ironed out. Further, due to the tremendous force applied to the materials, the porosity in the mold cavity is substantially decreased, resulting in a smoother, higher quality optical surface than was present on the original optical polished blank, and the deformation of the blank material work hardens the metal, resulting in a harder, more durable surface.

Figure 10:
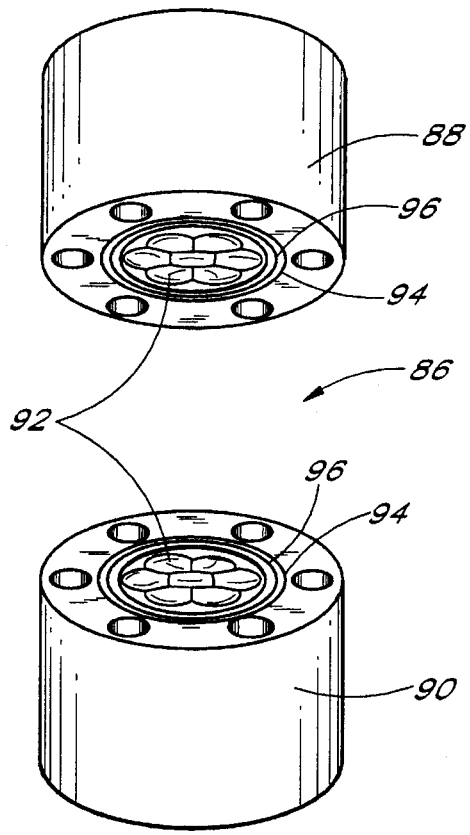
FIG. 10 is an exploded perspective view of a two-piece mold capable of forming a multi-faceted intraocular lens.

In order to form the flat, flexible intraocular lens of the present invention, a mold 86, as illustrated in FIG. 10, comprising an upper mold half 88 and a lower mold half 90 is utilized. Each of the mold halves 88, 90 comprises a mold cavity 92 having a plurality of cavities therein to form the optical elements of the lens. Each of the cavities in the mold halves 88, 90 is formed utilizing the process described above. Once each of the mold halves 88, 90 is formed having a desired mold cavity 92, the eruptions surrounding the periphery of each cavity 92 must be ground off. Advantageously, each mold cavity 92 was pressed to a depth of approximately 0.1 to 0.5 mm. Preferably, this depth enables imperfections in the mold blank 61, as well as eruptions surrounding the periphery of each cavity 92 to be ground down and still have a mold cavity 92 of the desired depth. In order to protect the optical surface of the mold cavity 92 during subsequent processing, an adhesive backed disk, or other type of covering, having a light adhesive backing to prevent slippage and having a known thickness, is carefully placed on the surface of each mold cavity 92 during the grinding and machining processes. The face of each mold half 88, 90 is ground down until a final mold cavity depth of approximately 0.1 to 0.5 mm is attained.

With the adhesive backed disk still in place, an overflow groove 94 is machined using a lathe, around the periphery of each mold cavity 92. A thin ridge 96, referred to as the "mold shut-off", or "flash line", may be created intermediate the groove 94 and the respective mold cavity 92 so that concentric circles are formed around the mold cavity 92. The flash line 96 defines the outer limits of the molded lens. In order to ensure proper alignment of the mold halves 88, 90 during the molding process, a pair of alignment dowel pins (not shown) are secured to the bottom half 90 of the mold 86 in a conventional manner. Associated mating holes (not shown) are provided in the top half 88 of the mold 86 to receive and retain the dowel pins during the molding process.

The upper and lower halves 88, 90 of the mold 86 are relatively movable towards and away from each other to allow the introduction of material which will form the optical element therein. Preferably, the lenses are produced via compression molding, although other molding processes, such as injection molding, may also be employed. Silicone, in a liquid form having a volume somewhat greater than that of the sum of the volumes of each of the mold cavities 92 in the upper and lower mold haves 88 and 90, is introduced into the cavity 92 of the lower mold half 90. Preferably, about 25 ml of uncured liquid silicone polymer is used to form the lens, however, this may vary from 5 ml–75 ml depending on the lens diopter and the configuration of the lens. The upper half 88 of the mold 86 is then brought into engagement with the lower half 90 of the mold 86, so that the alignment dowel pins are met by the associated mating holes. Once the mold 86 is closed, the excess volume of silicone will leak out between the molded pans and into the overflow grooves. The mold 86 is then heated for a predetermined time at an elevated predetermined temperature that will polymerize the monomers located therein into a solid polymer. In a preferred embodiment, the mold 86 is heated for about 10 minutes at 300° F. Following the polymerization of the lens material, the mold 86 is opened, and the lens is removed therefrom.

A small amount of flash created during the production of the lens at the flash line will be sporadically disposed about the edge of the lens. Significantly, there is only one flash line on the just formed lens. The lens is tumbled to remove the flash from the periphery of the lens and to polish the edges thereof. Preferably, a tumbler is filled with 1 mm to 6 mm glass beads, isopropyl alcohol, and fumed silicon dioxide. Typically, fumed silicon dioxide is used as the polishing agent when tumbling silicone lenses to accelerate the tumbling process. When using fumed silicon dioxide as a polishing agent in a water medium, the silicone lenses tend to float out and not polish. Isopropyl alcohol, however, has a lower surface tension than water, and a lower specific gravity than silicone, and will allow the lenses to sink, thereby making it an ideal tumbling matrix. The isopropyl alcohol has another advantage, in that the silicone lens material absorbs a portion of the alcohol, causing the lenses to uniformly swell an average of 7 percent, which in turn lowers the tear strength of the lens material. As the tear strength decreases, the abrading process, caused by the tumbling action of the tumbler, is further accelerated. The tumbling process tends to abrade more rapidly at the lip or margins of the lens. In addition, the flash, created during the production of the lens in the area where the two mold halves met, substantially disappears after tumbling, leaving a lens having a blended, radiused edge. In addition, a thick layer of fumed silicon dioxide will be present on the outer surface of the lens. It has been found that this residue improves subsequent adhesive bonding of the haptic to the lens. If haptics are being bonded to the lens element, the silicone dioxide residue is therefore left on the surface of the lens in the locations where haptic bonding is anticipated. The haptics are bonded to the lens utilizing conventional adhesive bonding techniques, however, any bonding techniques known to one of skill in the art can be utilized. The fumed silicon dioxide residue on the remaining outer surface of the lens, however, will be rinsed off using standard cleaning and extraction techniques. If haptics are not being bonded to the lens, the formed silicon dioxide residue is rinsed off the entire surface of the lens, as described above.

Figure 11:
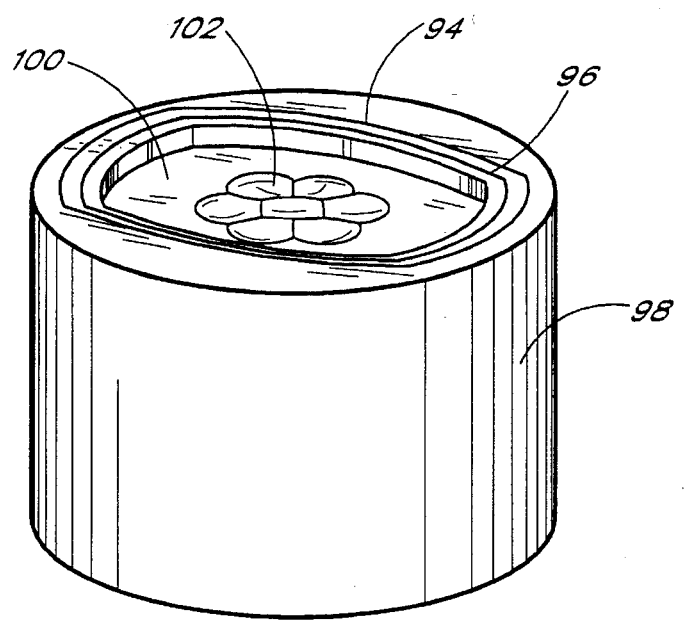
FIG. 11 is a perspective view of one-half of a two-piece mold capable of forming a single-piece multi-faceted intraocular lens.

Referring to FIG. 11, a lower mold half 98 for a single-piece lens mold is illustrated. A haptic coining mandrel (not shown) having the shape a reverse imprint of a lower half of a desired haptic cavity 100 is pressed into the lower mold half 98 utilizing the mold cavity forming procedure described above in order to form the haptic cavity 100. Within the central portion of the haptic cavity, a coining mandrel 60 having the reverse impression of a desired optical surface 102 is pressed into the surface of the haptic cavity 100 in order to form the optical surface 102. As described above, a coining mandrel 60 having the same or different surface impression as the previous coining mandrel is pressed into the haptic cavity 100 until the surface impression 59 of the coining mandrel 60 is pressed into the haptic cavity 100, utilizing a hydraulic press or other pressure means, forming another optical surface 102. The impression of a coining mandrel 60 having the reverse imprint of the desired optical surface into the haptic cavity 100 is repeated until the desired optical surfaces are formed. The mold half 98 is ground down to the desired mold cavity depth as described above. In addition, the overflow groove 94 and flash line 96 are formed in the lower mold half 98. In order to form the flat, flexible and compressible intraocular lens of the present invention, an upper mold half is formed utilizing the process described above.

Figure 12:
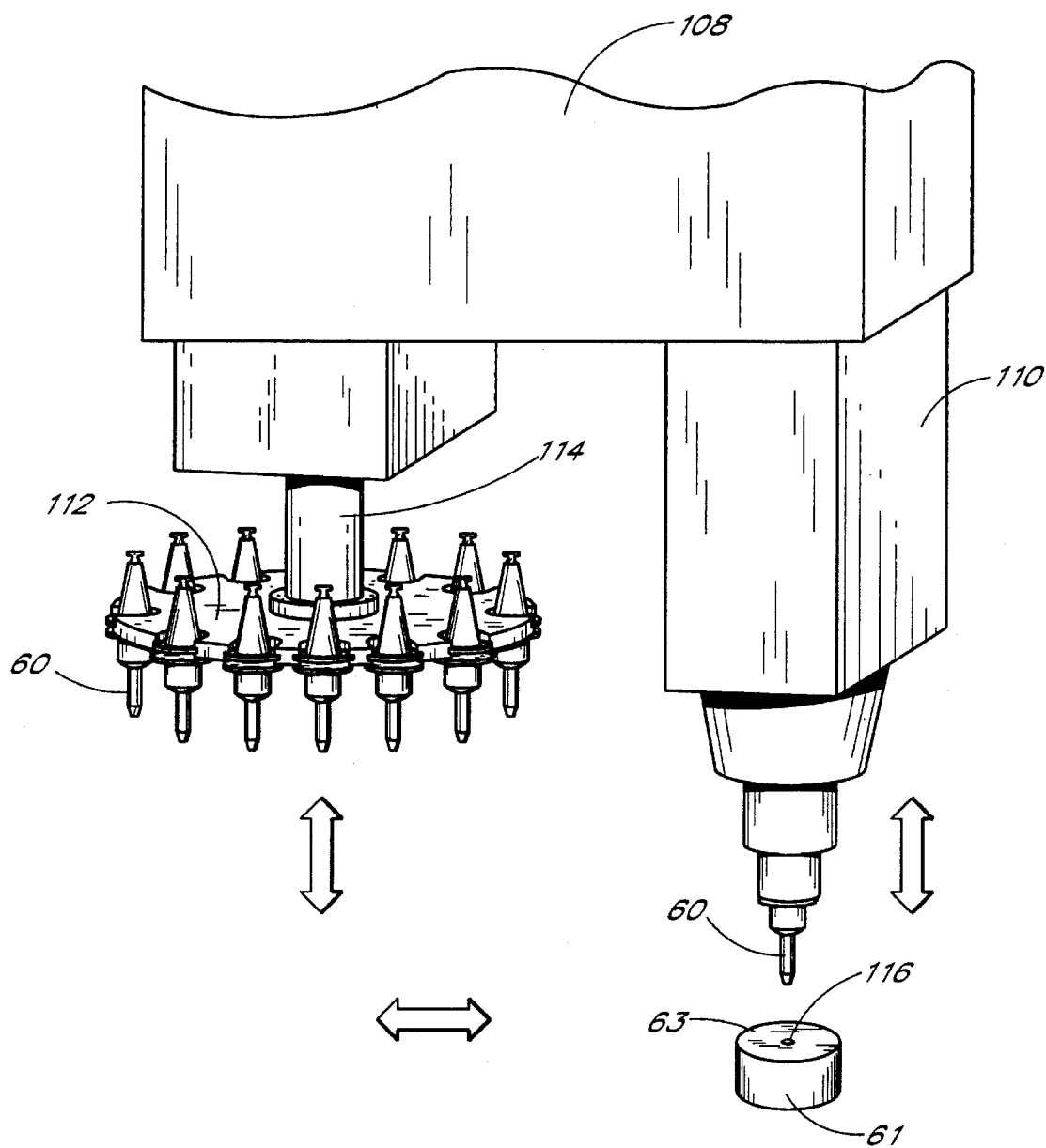
FIG. 12 is schematic perspective view of a CNC machine which is used to make the mold halves of the intraocular lens.

In another embodiment, as illustrated in FIG. 12, a CNC hydraulic press machine 108, comprising a head stock 110 and a tool carousel 112, can be used to form the impression of the coining mandrel 60 into the mold blank 61. Preferably, a plurality of coining mandrels 60, each having a different lens shape and/or optical power, are formed and placed in a tool carousel 112. The tool carousel 112 is located in proximity to the CNC machine head stock 110. The tool carousel 112 rotates around a central axis 114 and moves toward the head stock 110 to position the appropriate coining mandrel 60 in proximity to the head stock 110. The head stock 110 grasps the desired coining mandrel 60 and holds it firmly in place. The head stock 110 with the coining mandrel 60 in place is moveable in a Z-axis, i.e., up and down, to press the coining mandrel 60 into the mold blank 61 below. The head stock 110 presses the coining mandrel 60 into the mold blank 61 with a sufficient force to deform the surface of the mold blank 61 with the surface impression 116 of the coining mandrel 60. This coining mandrel selection and impression into the mold blank 61 can be repeated to achieve the desired pattern on the mold blank. This process may include the selection of one or more coining mandrels 60 having differing lens shapes and diopter powers which are pressed into the mold blank 61 to form the desired lens design. Further, the mold blank 61 used to form the upper mold half may have a completely different design pressed into it by the CNC machine 108 than the mold blank 61 used to form the lower mold half of the same mold. Advantageously, the CNC machine 108 greatly simplifies the process of coining mandrel selection and mold impression. The CNC machine 108 is easily programmable by those of skill in the art to form a number of mold blanks with a variety of optical configurations and diopter powers.

Figure 13:
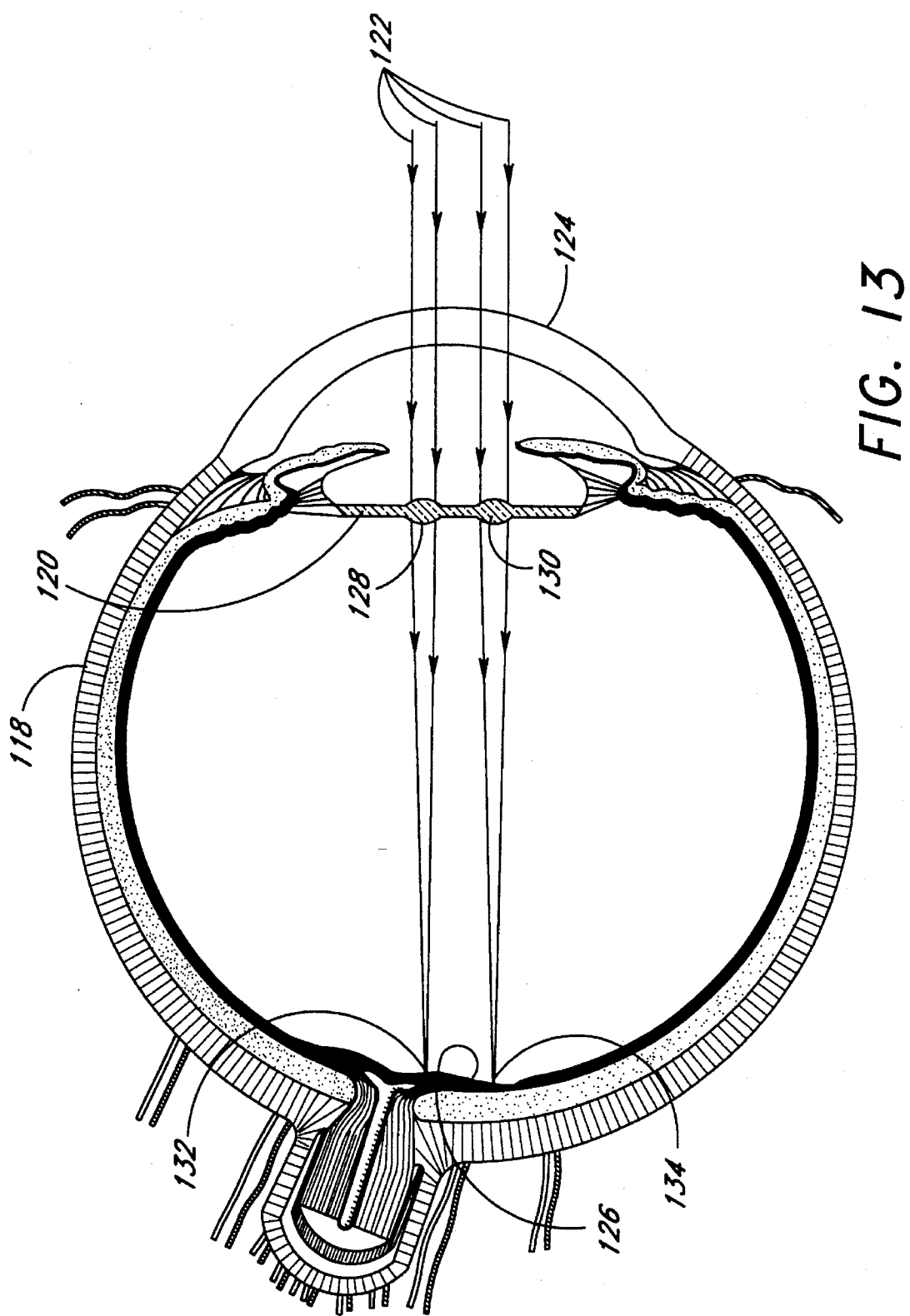
FIG. 13 is a cross-sectional view of an eye with an intraocular lens comprising two optical elements.

FIG. 13 is a cross-sectional view of an eye 118 with a multi-faceted intraocular lens 120 implanted therein. The arrows represent the direction of the light rays 122 as they are first focused by a cornea 124 and subsequently focused by the intraocular lens 120 onto a retina 126 of the eye 118. As discussed above, the light rays 122, as they pass through the cornea 124 of the eye, are prefocused. This prefocusing results in an approximate convergent conical angle of 12 degrees. The light rays 122 incident on each of a first and second optical elements 128, 130, respectively, of the multifaceted intraocular lens 120 are focused onto the retina 126 of the eye 118. Each of the optical elements 128, 130 focus the light onto different portions of the retina 126. As illustrated in FIG. 13, a first optical element 128 focuses the light on a central portion 132 of the retina 126, while the second lens element 130 focuses the light on a noncentral portion 134 of the retina 126.

A multi-faceted intraocular lens, such as the intraocular lens 120 illustrated in FIG. 13, can be advantageously used to correct a number of visual problems of the eye, such as AMD, retinitis pigmentosa (RP) or other retinal based visual impairing diseases, depending upon the number and placement of the optical elements on the intraocular lens 120. In addition, a multi-faceted intraocular lens, such as the intraocular lens 120 illustrated in FIG. 13, can be advantageously used to correct focal problems common in cataract related lens replacements. In those patients suffering from retinal damage, such as AMD and RP, a central portion of the retina 126 is damaged. In one embodiment of the multifaceted intraocular lens 120, a first optical element 128 is positioned and aligned to form an image on a first location 132 on a retina of a patient and a second optical element 130 is positioned and aligned to form an image on a second location 134 on a retina of a patient as illustrated by the light rays 122 on the drawing. Preferably, at least one of the locations on the retina, such as the second location 134, is on a non-central portion 134 of the retina. Therefore, one method of treating AMD comprises providing a patient with a multifaceted intraocular lens 120, as described above. The multi-faceted intraocular lens 120 is inserted into an eye 118 of the patient replacing his natural crystalline lens. One method of treating age-related macular degeneration, comprises the steps of transferring plural images of an object onto different locations on the retina 126. In a preferred embodiment, at least one of said plural images of said object is transferred onto non-central portion of the retina 126. By transferring the image onto plural locations of the retina 126, the healthy portions of the retina 126, such as the noncentral portions, preferably receive at least one of the transferred images from the intraocular lens 120. These functioning noncentral portions of the retina 126 will be able to collect and transmit visual information to the patient's visual interpretation system.

Therefore, the intraocular lens illustrated in FIG. 13 can advantageously be used to correct problems associated with AMD. The second optical element 130 of the intraocular lens 120 advantageously focuses the image onto a second location 134 of the retina 126, which is a noncentral portion of the retina 126, which in most cases has not been damaged. These noncentral portions of the retina 126 will be able to collect the light and transmit information to the brain. The image transferred by the first optical element 128 will be incident on the first portion 132 of the retina 126, which is in the central portion of the retina 126, as in the case of the normal crystalline lens of the patient, and this damaged portion of the retina 126 will be unable to collect and transmit information to the brain. Advantageously, by transmitting the image onto a non-central portion of the retina 126 that is able to collect the refracted image and send the information to the brain, the patient's vision will be improved.

Figure 14:
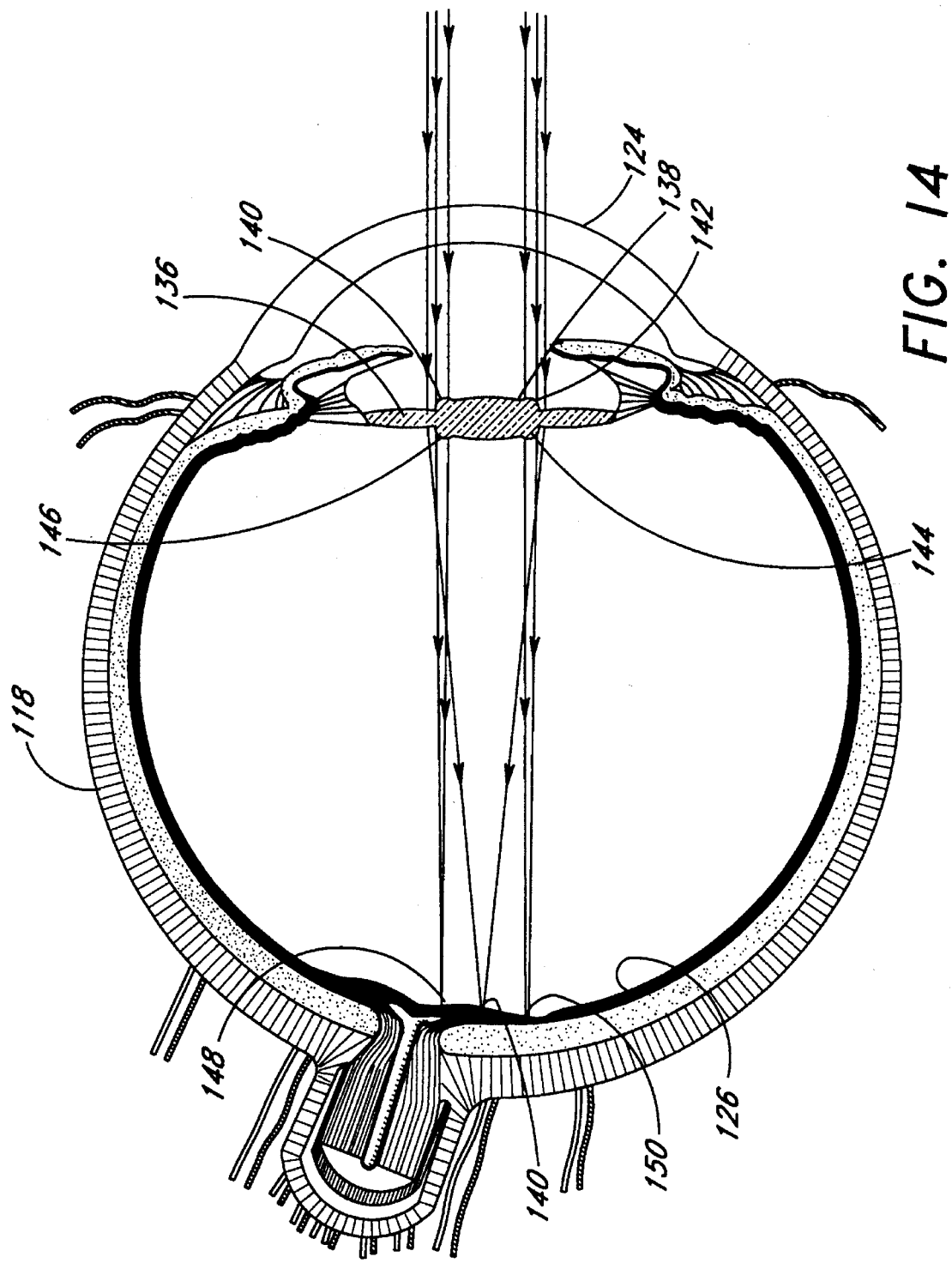
FIG. 14 is a cross-sectional view of an eye having a biconvex intraocular lens comprising four optical elements.

FIG. 14 illustrates a cross-sectional view of the eye 118 with another alternative embodiment of the intraocular lens 136 inserted therewithin. The illustrated embodiment of the intraocular lens 136 comprises a biconvex main lens element 138 illustrated with a plurality of optical lens elements 140–146 provided on both sides of the main lens element 138. As the light rays enter the cornea 124, they are prefocused onto the intraocular lens 136. Those light rays that are incident on the main lens element 138 of the intraocular lens 136 are focused onto central portion 140 of the retina 126. The light rays that are incident upon optical elements 140 and 146 are transferred to a first alternative location 148 of the retina 126. The light rays that are incident upon optical elements 142 and 144 of the intraocular lens 136 are transferred to a second alternative location 150 of the retina 126. Both the main lens element 138 and the optical elements 140-146 thereon each focus the light incident upon it to a different location on the retina 126, thereby providing a plurality of images for the brain to interpret. Therefore, if any portion of the retina 126 is damaged, it is more likely that one of the images will be incident upon a portion of the retina that is healthy. Additionally, the main portion of the lens body may be used to focus on far objects, whereas the optical elements may be used to focus on near objects. The distant and close objects will be focused on different portions of the retina; however, it is believed that the brain will be able to integrate and interpret various images, even if the images are overlapping.

Figure 15:
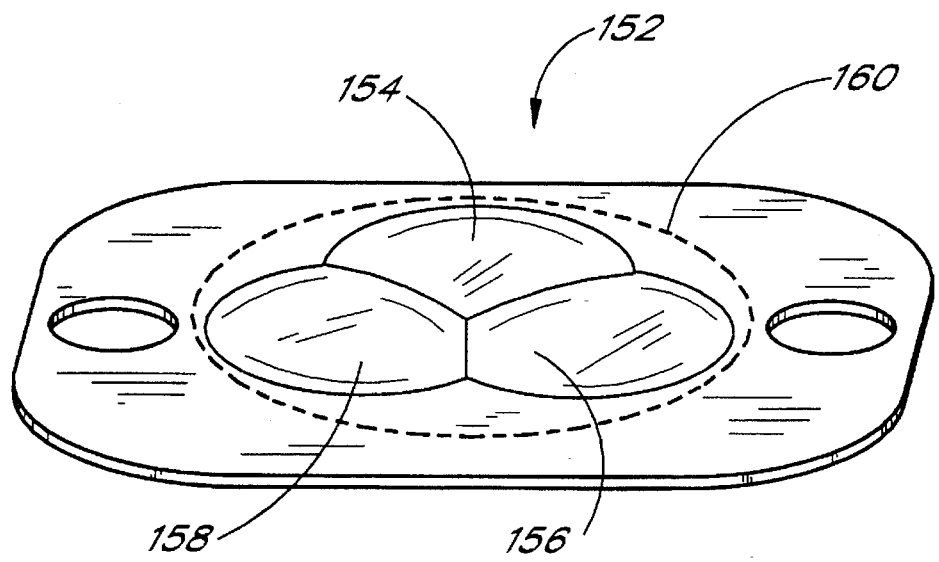
FIG. 15 is a perspective view of a single-piece intraocular lens comprising three intersecting optical elements having differing diopter powers.
Figure 16:
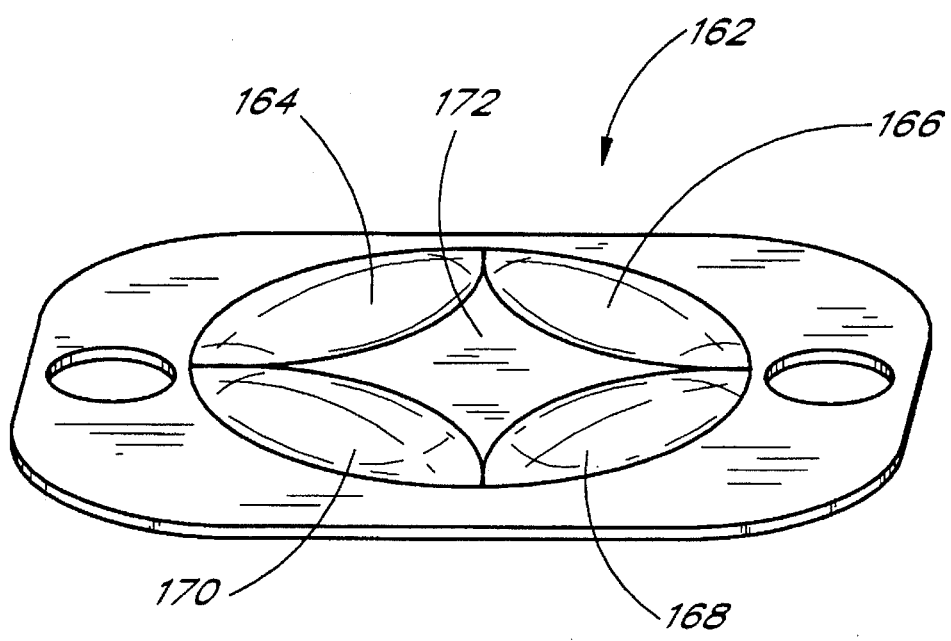
FIG. 16 is a perspective view of a thin, single-piece intraocular lens comprising four semi-spherical optical elements that are tangent to each other.

FIG. 15 illustrates an alternate embodiment of a flat, single-piece intraocular lens 152 with three lens element portions 154–158 located in a central portion 160 of the lens 152. Each of the lens element portions 154–158 are positioned to overlap each other in the central portion 160 of the intraocular lens 152. As illustrated in FIG. 16, it is not necessary that an entire or substantial circular portion of the lens element be provided. The alternate embodiment of the lens 162 illustrated in FIG. 16 comprises a plurality of semi-spherical lens elements 164–170, which are tangent to each other. A central portion 172 of the intraocular lens 162 does not provide for any alteration of the light rays that are incident thereupon.

Figure 17:
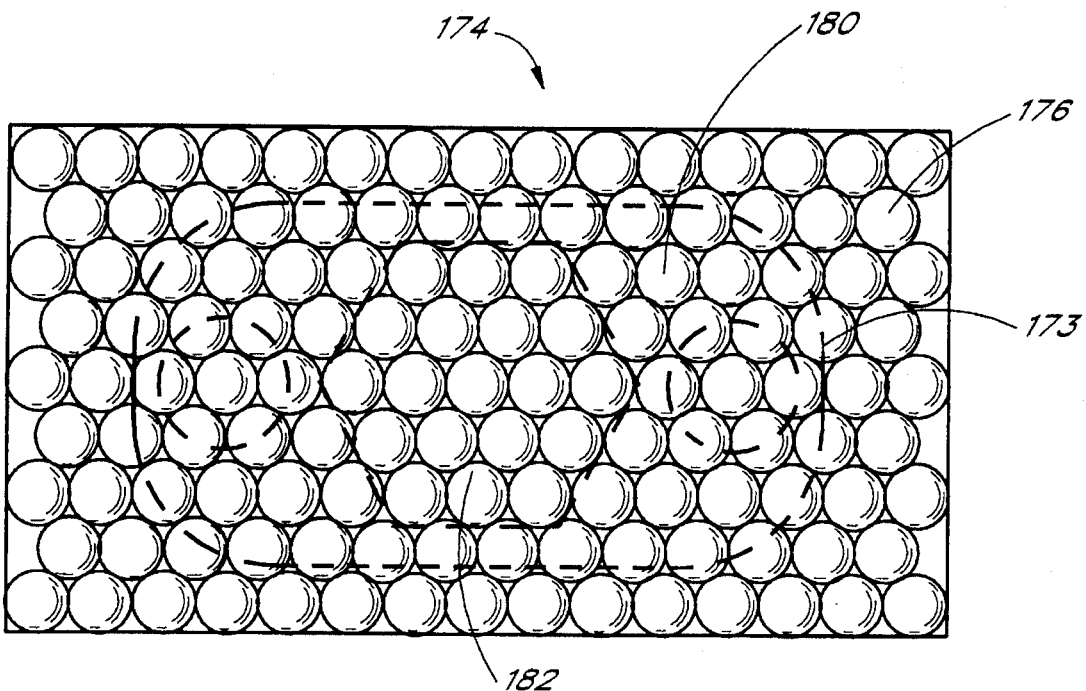
FIG. 17 is a top plan view of an intraocular lens made from a sheet of silicone comprising a plethora of optical elements having the same diopter power.

FIG. 17 illustrates still another alternate embodiment of a flat, single-piece intraocular lens 173 of the present invention. In this embodiment, a sheet of silicon material 174 is covered with a plethora of optical elements 176. Preferably, the desired shape of the intraocular lens 173 can be stamped from the large sheet 174. Despite the fact that the entire intraocular lens 173, including a haptic portion 180, is covered with lens elements 176, only a central portion 182 of the intraocular lens 173, as indicated by the dotted lines, will be within the patient's visual pathway. Preferably, each of the optical elements 176 on the silicone sheet 174 have the same lens shape and diopter power. Therefore, it is not necessary to specify a specific location on the sheet 174 where the intraocular lens 173 is formed. Preferably, a simple stamping process is utilized to cut a plurality of intraocular lenses 173 from the sheet 174. The number of intraocular lenses 173 which can be formed from the sheet 174 depends upon the size of the sheet 174 and the dimension of the intraocular lens 173. Utilizing the stamping process, the costs to manufacture the intraocular lens 173 are significantly less than those required to individually mold each lens. The sheet 174 of intraocular lens elements may be made from an extremely large mold, utilizing the procedure described above in association with forming a mold blank or may be manufactured by other plastic-forming procedures known to those of skill in the art. The stamped lens is then tumble polished as described above to blend and polish the sharp stamping edges.

Figure 18:
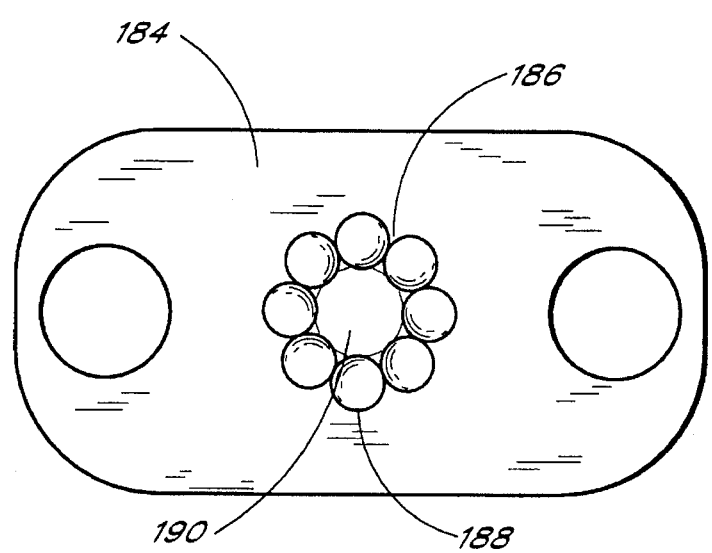
FIG. 18 is a top plan view of a single-piece intraocular lens having an annular ring of optical elements.
Figure 19:
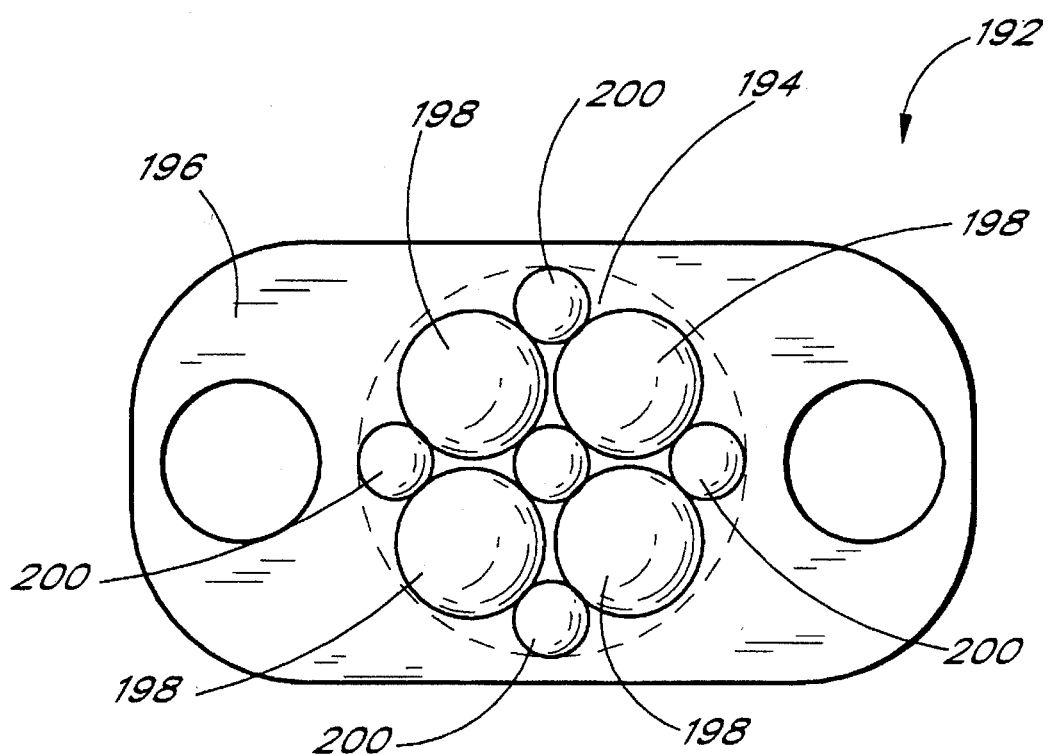
FIG. 19 is a top plan view of an intraocular lens having a plurality of optical elements of differing diopter powers.

FIG. 18 illustrates still another embodiment of the intraocular lens 184 comprising an annular ring 186 of lens elements 188. A central portion 190 within the annular ring 186 does not provide any alteration of the light rays incident thereupon. However, the light rays that are incident upon each of the optical lens elements 188 is in turn transferred onto a portion of the retina. The lens illustrated in FIG. 18 is similar to the lens illustrated in FIG. 6. In FIG. 6, the annular ring 56 of optical lens elements 16 is placed around the convex main optical element 52 of a convex lens 54, whereas the annular ring 186 of lens element portions 188, illustrated in FIG. 18, encircles a central portion 190, which does not provide any accommodation. FIG. 19 illustrates another embodiment of a thin, single-piece intraocular lens 192 having a central accommodation portion 194 and a haptic portion 196. The central accommodation portion 194 comprises a plurality of optical elements with a first plurality of optical elements 198 having a first diopter power P1 and a second plurality of optical elements 200 having a second diopter power P2. This alternate embodiment of the thin, single-piece intraocular lens 192 illustrates that the optical elements 198–200 may have various diopter powers and may be arranged in a variety of configurations to achieve the desired level of accommodation.

FIGS. 20–26 illustrate a plurality of embodiments of an intraocular lens of the present invention. The intraocular lenses comprise concave surfaces, convex surfaces, and nonconcave or nonconvex surfaces. As will be apparent to those of skill in the art, the intraocular lenses of the may be embodied in other specific forms without departing from its spirit or essential characteristics. These illustrated embodiments are to be considered in all respects only as illustrative and not restrictive.

In many of the single-piece intraocular lenses of the prior art a transition region is formed between the thick optical element and the haptic support portion. This transition region forms an obtuse-angle junction between the two portions of the single-piece lens which may result in the occurrence of "the cusp effect". The obtuse-angle junction transfers the light rays incident upon the transition region into a blinding halo around the patient's filed of vision. Normally, adding additional optical elements to the lens would result in these blinding halos forming around each of the optical elements portions.

Figure 27:
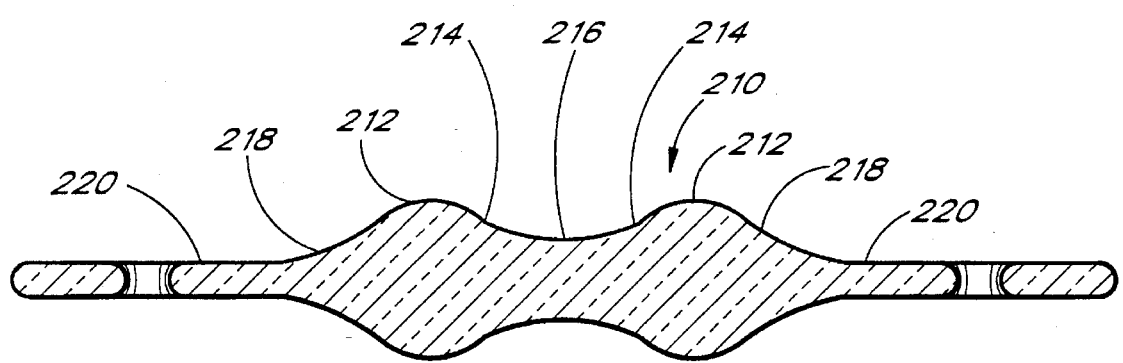
FIG. 27 is a cross-sectional view of a concave optical element on a main optical element illustrating the smooth transition region between the optical element and the main optical element.

Advantageously, by forming the multi-faceted intraocular lens 210 in a mold in which the shape of the optical elements 212 have been coined into the mold surface as described above, a smooth transition region 214 between the optical element 212 and the main optic 216 results, as illustrated in FIG. 27. In addition, the coining process causes a smooth transition region 218 to occur between the optical elements 212 and the haptic 220. Without the sharp-corner transition between the optical elements 212 and the haptic 220 and between the optical elements 212 and the main optic 216, the "cusp effect" is eliminated around each of the optical elements 212, as there is no well-defined surface at the transition regions 214, 218 for light to refract into the eye of the patient. In addition, the absence of the sharp-corner transitions between the optical elements 212 and the main optic 216 as well as between the optical elements 214 and the haptic 220 causes the lens to be less likely to suffer damage during insertion, especially when the lens is inserted through a conventional lens injector. The smooth transition region between the optical elements 212 and the main optic 216 forms a stronger connection between the optical elements 212 and the main optic 216 reduces stresses and forms a stronger connection which is less likely to tear or become damaged during loading into a lens injector, such as the injector, illustrated in FIG. 2.

In addition, many intraocular lens patients have commented that they are unable to focus on both near and distant objects. Advantageously, in a preferred embodiment of the intraocular lens of the present invention, as described above, the optical elements of the main optic may be aligned to form a multi-focal lens. In one embodiment, an optical element of a conventional biconvex spherical lens additionally comprises an annular ring of optical elements on one side of the main optical element. The annular ring of optical elements is used to provide a multi-focal lens by focusing all of the light rays that are incident on the annular ring of optical elements to the same focal point and by focusing all of the light rays which are incident upon a center of the main optical element to another focal point, thereby enabling the wearer to focus on both close and distant objects.

Finally, the required thickness of the optical elements are such that the profile of the intraocular lens of the present invention can be greatly reduced over the profile of the intraocular lenses of the prior art. The reduction in thickness of the optical element of the single-piece flexible lens as described above can be adapted with optical elements positioned to provide a number of different types of vision correction and enables the insertion of the single-piece intraocular lens through a substantially smaller opening, such as a 1 mm–4 mm opening, than in the prior art.

The present invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within their scope.

What is claimed is:

1. An intraocular lens for implantation in a human eye, comprising: a monolithic optical portion comprising a main body portion having a surface and plural lens portions, each having separate optical axes and each formed as an extension of the surface of said main body portion; and a main body portion;

a haptic portion extending outwardly from said main body portion; and said one-piece lens formed of resilient material which permits said main body portion, said haptic portion, and said plural lens portions to assume their original shapes after said one-piece lens is rolled upon itself for implantation into said eye.

2. The intraocular lens of claim 1, wherein the optical portion and the haptic portion are monolithic.

* * * * *

UNITED STATES PATENT AND TRADEMARK OFFICE
CERTIFICATE OF CORRECTION

PATENT NO.    : 5,507,806  
DATED         : April 16, 1996  
INVENTOR(S)   : Larry W. Blake Page 1 of 1

It is certified that error appears in the above-identified patent and that said Letters Patent is hereby corrected as shown below:

<u>Column 17, line 8 through Column 18, line 8,</u>  
Delete Claim 1 in its entirety and replace with the following text:

-- 1. An intraocular lens for implantation in a human eye, comprising:
    a monolithic optical portion comprising:
        a main body portion having a surface; and
        plural lens portions, each having separate optical axes and each formed as an
    extension of the surface of said main body portion, and
    a haptic portion extending outwardly from said main body portion;
    said lens formed of resilient material which permits said main body portion, said haptic portion, and said
        plural lens portions to assume their original shapes after said lens is rolled upon itself for
        implantation into said eye.

--

Signed and Sealed this

Ninth Day of September, 2003

JAMES E. ROGAN  
*Director of the United States Patent and Trademark Office*